(12) United States Patent
Greatbatch et al.

(10) Patent No.: US 6,909,915 B2
(45) Date of Patent: Jun. 21, 2005

(54) HYBRID BATTERY POWER SOURCE FOR IMPLANTABLE MEDICAL USE

(75) Inventors: Wilson Greatbatch, Akron, NY (US); Jeffrey Deal, Clarence, NY (US)

(73) Assignee: GentCorp Ltd., Lancaster, NY (US)

( * ) Notice: Subject to any disclaimer, the term of this patent is extended or adjusted under 35 U.S.C. 154(b) by 75 days.

(21) Appl. No.: 10/350,921

(22) Filed: Jan. 24, 2003

(65) Prior Publication Data

US 2004/0147971 A1 Jul. 29, 2004

(51) Int. Cl.$^7$ .................................................. A61N 1/40
(52) U.S. Cl. .......................................... 607/5; 320/103
(58) Field of Search ................................ 320/103–104; 607/5, 29

(56) References Cited

U.S. PATENT DOCUMENTS

| | | | |
|---|---|---|---|
| 3,941,135 A | * 3/1976 | von Sturm et al. | 607/35 |
| 3,959,706 A | 5/1976 | Mabuchi et al. | 320/2 |
| 4,119,103 A | 10/1978 | Jirak | 128/419 |
| 4,548,209 A | 10/1985 | Wielders et al. | 128/419 |

(Continued)

FOREIGN PATENT DOCUMENTS

| WO | WO9622811 | 8/1996 | A61N/1/39 |
|---|---|---|---|

OTHER PUBLICATIONS

"Simulation of capacity fade in lithium–ion batteries"; R. Spotnitz; Journal of Power Sources 113 (2003) 72–80; 9 pages.

"Calendar and cycle–life studies of advanced technology development program generation 1 Lithium–ion batteries" R.B. Wright et al.; Journal of Power Sources 110 (2002) 445–470; 26pages.

"Improve Battery Performance with Proper Charging methods"; Isidor Buchmann; Medical Electronics Manufacturing Fall 2003; 4 pages.

*Primary Examiner*—Mark Bockelman
(74) *Attorney, Agent, or Firm*—Walter W. Duft

(57) ABSTRACT

A hybrid battery power source for implantable medical use provides relatively stable resistance during discharge and avoids the voltage delays that develop as a result of variable resistance increase in Li/SVO cells. The hybrid battery power source utilizes two batteries or cells, one being a primary battery of relatively high energy density and the other being a rechargeable secondary battery of low relatively stable internal resistance. The primary and secondary batteries are connected in a parallel arrangement, preferably via an intermediate voltage boost circuit having an inductor and a pulse generating control circuit therein. The energy storage capacitors of the medical device in which the hybrid battery power source is situated are driven in whole or substantial part by the secondary battery. The primary battery is used to as an energy source for recharging the secondary battery. By arranging the two batteries in parallel, with one serving as a primary battery and the other as a rechargeable secondary battery, all the benefits of the defibrillatory impulse will be obtained and the deficiencies arising from variable voltage delay found in prior art implantable power sources will not be present.

30 Claims, 3 Drawing Sheets

U.S. PATENT DOCUMENTS

| | | | |
|---|---|---|---|
| 4,736,150 A | 4/1988 | Wagner | 320/21 |
| 4,800,883 A | 1/1989 | Winstrom | 128/419 |
| 5,107,834 A | 4/1992 | Ideker et al. | 128/419 |
| 5,180,642 A | 1/1993 | Weiss et al. | 429/90 |
| 5,199,429 A | 4/1993 | Kroll et al. | 128/419 |
| 5,235,979 A | 8/1993 | Adams | 607/5 |
| 5,306,291 A | 4/1994 | Kroll et al. | 607/5 |
| 5,332,631 A | 7/1994 | Abraham et al. | 429/48 |
| 5,334,219 A | 8/1994 | Kroll | 607/5 |
| 5,372,605 A * | 12/1994 | Adams et al. | 607/5 |
| 5,383,907 A | 1/1995 | Kroll | 607/5 |
| 5,405,363 A * | 4/1995 | Kroll et al. | 607/5 |
| 5,407,444 A | 4/1995 | Kroll | 607/5 |
| 5,458,997 A | 10/1995 | Crespi et al. | 429/219 |
| 5,591,212 A | 1/1997 | Keimel | 607/5 |
| 5,620,464 A | 4/1997 | Kroll et al. | 607/5 |
| 5,674,248 A | 10/1997 | Kroll et al. | 607/5 |
| 5,836,973 A | 11/1998 | Kroll | 607/5 |
| 5,861,006 A | 1/1999 | Kroll | 607/5 |
| 5,899,923 A | 5/1999 | Kroll et al. | 607/5 |
| 5,904,705 A | 5/1999 | Kroll et al. | 607/5 |
| 6,180,283 B1 | 1/2001 | Gan et al. | 429/215 |
| 6,204,634 B1 | 3/2001 | Zimmerman et al. | 320/128 |
| 6,245,464 B1 | 6/2001 | Spillman et al. | 429/332 |
| 6,385,056 B1 * | 5/2002 | Gucyski | 363/15 |
| 6,426,628 B1 | 7/2002 | Palm et al. | 324/427 |
| 6,444,360 B2 | 9/2002 | Gan et al. | 429/215 |
| 6,549,807 B1 * | 4/2003 | Kroll | 607/34 |
| 6,552,511 B1 | 4/2003 | Fayram | 320/103 |
| 6,744,152 B2 * | 6/2004 | Kroll | 307/66 |
| 2003/0155887 A1 | 8/2003 | Bourilkov et al. | 320/104 |

\* cited by examiner

HYBRID BATTERY POWER SOURCE FOR IMPLANTABLE MEDICAL USE

BACKGROUND OF THE INVENTION

1. Field of the Invention

The present invention relates to improvements in the performance of implantable defibrillators, implantable cardioverter-defibrillators (ICDs) and other battery powered medical devices designed to provide high energy electrical stimulation of body tissue for therapeutic purposes.

2. Description of Prior Art

High energy battery powered medical devices, such as implantable defibrillators and ICDs, are designed to produce a strong electrical shock to the heart when called upon to correct the onset of tachyarrhythmia. The shock is produced by one or more energy storage capacitors that have been charged by the device's battery power source. This power source is typically a lithium/silver vanadium oxide (Li/SVO) battery or cell of the type disclosed in U.S. Pat. No. 5,458,997 of Crespi, and references cited therein. Crespi notes that the Li/SVO cell chemistry is useful for defibrillation applications because of its ability to produce pulses of energy that can charge the high voltage capacitors within the short time frame required by the device. In particular, the Li/SVO battery is typically called upon to charge the capacitors to deliver within 10 seconds or less a shock of up to 40 Joules. This must be done several times in succession if additional shocks are required. Unfortunately, as noted by Crespi, an Li/SVO cell can experience unpredictable resistance increase upon long-term discharge during service. In particular, Li/SVO cells commonly have a two-stage run down with slightly different voltage plateaus at each stage. It is at the interval between the two plateaus where it is common to see the resistance increase described by Crespi. The problem is further explained in U.S. Pat. No. 6,426,628 of Palm et al. as a being transient phenomenon that occurs following a period of low current draw. When a load is reapplied (e.g., a defibrillation pulse is required), the resistance build-up temporarily prevents the cell from developing its full open circuit voltage potential. This condition, which is referred to as "voltage delay," continues for a brief period until the resistance diminishes back to some nominal level.

In many cases, the voltage delay experienced by an Li/SVO cell is significant enough to impair the cell's ability to charge the capacitors of a defibrillator or ICD in a timely manner. This may result, prematurely, in a decision being made that the Li/SVO cell has reached end of service (EOS) and needs to be explanted for replacement. In addition to the patient inconvenience and risk entailed by this procedure, a significant portion of the capacity of the Li/SVO cell is needlessly rendered unavailable for long-term use. Even if it is not removed, the cell's operation is unpredictable, thus making any attempt to calculate the EOS point rather complicated.

A need therefore exists for an improvement in defibrillator/ICD battery power systems so as to mitigate the aforementioned characteristics of Li/SVO cells. What is required is an implantable power source with increased stability and whose operation is more predictable as a basis for simple EOS determination.

SUMMARY OF THE INVENTION

The foregoing problems are solved and an advance in the art is provided by a novel hybrid battery power source for high energy battery powered medical devices, such as implantable defibrillators and ICDs. The hybrid battery power source has relatively constant charge time characteristics and is not affected by the voltage delay phenomenon associated with Li/SVO batteries. In exemplary embodiments of the invention, the power source utilizes two batteries, each of which may comprise one or more cells. The first battery is a primary (nonrechargeable) battery of relatively high energy density. The second battery is a secondary (rechargeable) battery whose internal resistance is relatively low and stable over time. The primary and secondary batteries are connected in a parallel arrangement, preferably via an intermediate voltage boost circuit having an inductor and a pulse generating control circuit therein. The defibrillatory charge circuit output of the power source is provided in whole or substantial part by the secondary battery. The primary battery is used as an energy source for the secondary battery. By arranging the two batteries in parallel, with one being a primary battery and the other being a rechargeable secondary battery, all the benefits of the defibrillatory impulse will be obtained and the deficiencies arising from variable resistance increase will not be present.

It is therefore an object of the invention to minimize the effect of the change in resistance as a battery for implantable medical use runs down during service.

A further object of the invention is to add a low resistance secondary segment to an implantable power source that will provide a source for rapid charging of energy storage capacitors used to delivery high-energy impulses.

A still further object of the invention is to utilize a primary segment of an implantable power source to recharge a secondary rechargeable segment of the power source during intervals between defibrillator pulses.

A still further object of the invention is to minimize the variability of charge time due to a conventional battery for implantable defibrillator and ICD use by employing a battery whose characteristics provide negligible charge time variance.

BRIEF DESCRIPTION OF THE DRAWINGS

The foregoing and other features and advantages of the invention will be apparent from the following more particular description of preferred embodiments of the invention, as illustrated in the accompanying Drawings in which.

DETAILED DESCRIPTION OF PREFERRED EMBODIMENTS

Introduction

Figure 1:
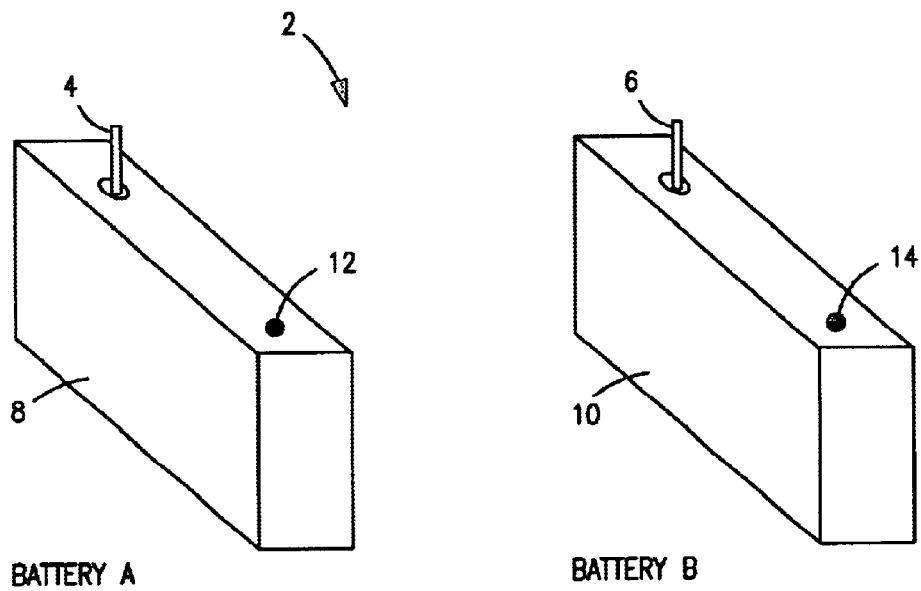
FIG. 1 is a diagrammatic perspective view showing primary and secondary batteries in accordance with the invention.

Exemplary hybrid battery power sources for use with implantable defibrillators, ICDs and other high energy battery powered medical devices will now be described, together with an exemplary defibrillator that incorporates a hybrid battery power source therein. As indicated by way of summary above, the power source embodiments disclosed herein are characterized by having primary and secondary batteries. The primary battery has high energy density but will typically also have an internal resistance that is relatively high, or which can increase significantly during rundown. Examples include the lithium-silver vanadium oxide (Li/SVO) battery and the lithium-carbon monofluoride (Li/CFx) battery. The secondary battery is rechargeable and has low internal resistance that is relatively stable over time. It will typically also have relatively low energy density. Examples include the lithium-ion battery. The primary and secondary batteries are electrically connected in parallel arrangement, either directly or indirectly through a voltage boost circuit.

In a direct parallel connection arrangement, the primary battery charges the secondary battery to the existing voltage of the primary battery, which for an Li/SVO battery averages about 2.6 volts and for an Li/CFx battery about 2.5 volts. The normal maximum voltage of a lithium-ion rechargeable battery is about 4 volts. Thus, a lithium-ion secondary battery normally would not be charged to its full voltage by an Li/SVO or Li/CFx primary battery, but instead would be charged to the primary battery's lower voltage level. When defibrillation is demanded, a majority of the defibrillatory circuit charging energy will come from the secondary battery rather than the primary battery because the former will supply more current due to its lower internal resistance and lack of voltage delay. Once the defibrillatory cycle is ended, and if the secondary battery has dropped below the primary battery in voltage, the secondary battery will recharge from the primary battery back to the latter's existing voltage.

In an indirect parallel connection arrangement of the primary and secondary batteries, a voltage boost circuit is interposed to increase and control the voltage supplied by the primary battery to the secondary battery. The boost circuit operates independently of primary battery run-down. For example, in a hybrid battery power source comprising an Li/SVO primary battery and a lithium-ion secondary battery interconnected by a voltage boost circuit, the principal energy supplied by the Li/SVO battery at about 2.6 volts can be increased to charge the lithium-ion battery to its normal open circuit voltage of about 4 volts. This charging voltage can be sustained even as the Li/SVO battery voltage output varies during service. The voltage boost circuit also ensures that virtually all of the defibrillatory charging energy comes from the secondary battery. In this way, the primary battery is used as a long term energy supply to recharge the secondary battery for service when and if its voltage drops below the desired level. The defibrillatory impulses will have the characteristics of the secondary battery.

The hybrid power source embodiments disclosed herein can be designed for maximum service life by selecting the primary and secondary batteries so that the former provides most of the combined battery capacity while still allowing the latter to power a reasonable number of defibrillatory cycles prior to requiring recharge, say 100 cycles. By way of example, the secondary battery could be selected to provide 10% of the total capacity of power source, with the primary battery providing the remaining 90%.

If an implantable defibrillator or ICD is provided with an Li/SVO primary battery and a lithium-ion secondary battery arranged in the manner disclosed herein, the lithium-ion battery will be the predominant energy source for charging the defibrillator's energy storage capacitors during the defibrillation cycle. Since this battery would always be charged to the same voltage level between discharges, regulation of the Li/SVO battery would not be a factor. The system would utilize the superior energy storage capabilities of the Li/SVO battery, but would be able to ignore the resistance increases that can develop during Li/SVO run down. This is especially true if a voltage boost circuit is used because the boost circuit would always raise the charging voltage of the lithium-ion battery to the desired level regardless of the state of discharge of the Li/SVO battery down to its end-of-life voltage point. Thus, advantage can be taken of the superior properties of the Li/SVO battery, while enabling the manufacturer to ignore the variable resistance characteristics thereof. The manufacturer can rely on a lithium-ion battery having no voltage delay properties of its own, and relatively stable internal resistance, to drive the defibrillation impulses. Additionally, the use of a voltage boost circuit in conjunction with the lithium-ion battery would provide a power source with a higher operating voltage than would be possible with an Li/SVO battery alone. This provides a significant advantage in efficiency for the defibrillator charging circuitry because the higher input voltage mitigates the effects of circuit resistance losses which would result from the higher operating currents required at lower operating voltages.

Illustrated Embodiments

Turning now to the Drawings wherein like reference numerals signify like elements in all of the several views, FIG. 1 illustrates two segments of a hybrid battery power source 2, namely, a primary battery "A" and a secondary battery "B". By way of example only, the primary battery "A" will be assumed to incorporate either an Li/SVO or Li/CFx battery chemistry, and the secondary battery "B" will be assumed to incorporate a rechargeable lithium-ion battery chemistry. Such batteries are standard commercial items that available from Wilson Greatbatch Technologies, Inc. of Clarence, N.Y. as catalog items. FIG. 1 also depicts that for each of battery "A" and battery "B," one electrical connection can be made via the vertical pins 4 and 6 respectively protruding from the top of the cases 8 and 10. The pins 4 and 6 represent the positive (cathode) terminals of the batteries. A second electrical connection can be made to the cases 8 and 10 themselves, and case contacts 12 and 14 are respectively shown. These case contacts represent the negative (anode) terminals of the batteries.

Figure 2:
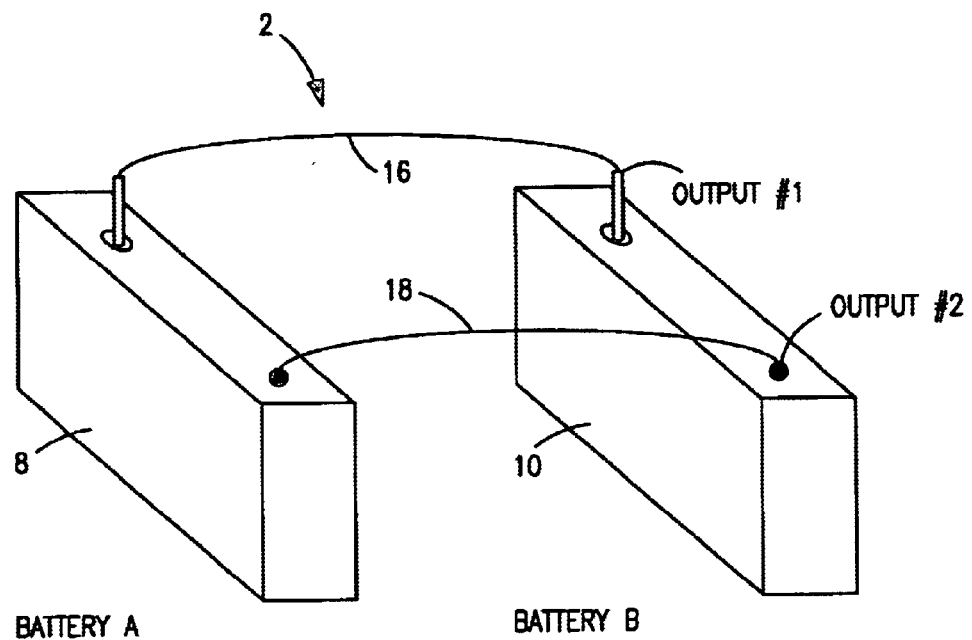
FIG. 2 is a diagrammatic perspective view showing an exemplary hybrid battery power source comprising the batteries of FIG. 1 connected directly in parallel.

FIG. 2 is similar to FIG. 1 in that the hybrid battery power source 2 and its two batteries "A" and "B" are depicted. In FIG. 2, however, the battery electrical terminals are connected at 16 and 18 in a parallel configuration (positive to positive, negative to negative) so that an electrical load (e.g., a defibrillator charging circuit) can be connected across the leads labeled "Output #1" and "Output #2." The hybrid battery power source 2 is a very simple embodiment of the invention comprising nothing more than the two batteries "A" and "B" connected in parallel. The function of the primary battery "A" is to recharge the secondary battery "B" and to maintain its open circuit voltage equal to that of battery "A." The function of the secondary battery "B" is to power the load.

Upon the demand for a defibrillatory impulse, the current flow will cause the voltage of the parallel-connected batteries to fall, due to the respective internal resistances. The higher internal resistance of the primary battery "A" will limit the current that can be supplied to less than that of the secondary battery "B," so that the majority of the defibrillatory impulse would be supplied from the latter. After the end of the defibrillatory sequence, and over a longer period of time, the secondary battery "B" will recharge back up to the peak voltage of the primary battery "A."

If the primary battery "A" is an Li/SVO or Li/CFx battery, and the secondary battery "B" is a lithium-ion battery, both being sized for implantable use, the latter would typically have a capacity of approximately one tenth of the capacity of the two batteries "A" and "B" combined. Thus, the Li/SVO or Li/CFx battery will represent the primary energy reservoir of the hybrid battery power source 2. During a defibrillation cycle, the power source 2 will supply energy to the defibrillatory pulse-generating system, which will typically comprise a fly-back converter circuit that charges a pair of energy storage capacitors. The lithium-ion battery will provide a high current source for recharging the defibrillator's capacitors insofar as the internal resistance of the lithium-ion battery is lower than that of the Li/SVO or Li/CFx battery, and is relatively constant. This means that a greater proportion of the current flow would come out of the lithium-ion battery with an associated highly predictable charge time.

By way of example, if the lithium-ion battery is designed with a maximum current of about six amperes and is charged to about 2.5 volts, eight seconds of charge time will be sufficient to produce a 40 Joules pulse. An eight-second charge time is much lower than what is generally available from present day Li/SVO implantable defibrillator batteries. Thus, the hybrid facility of having a lithium-ion secondary battery, with its negligible voltage delay characteristics and six-ampere charge current providing an eight-second charge time, is a distinct improvement over previous defibrillator batteries. The Li/SVO or Li/CFx primary battery, with its higher internal resistance, will recharge the lithium-ion battery for some extended time that would not be critical to defibrillator function.

Figure 3:
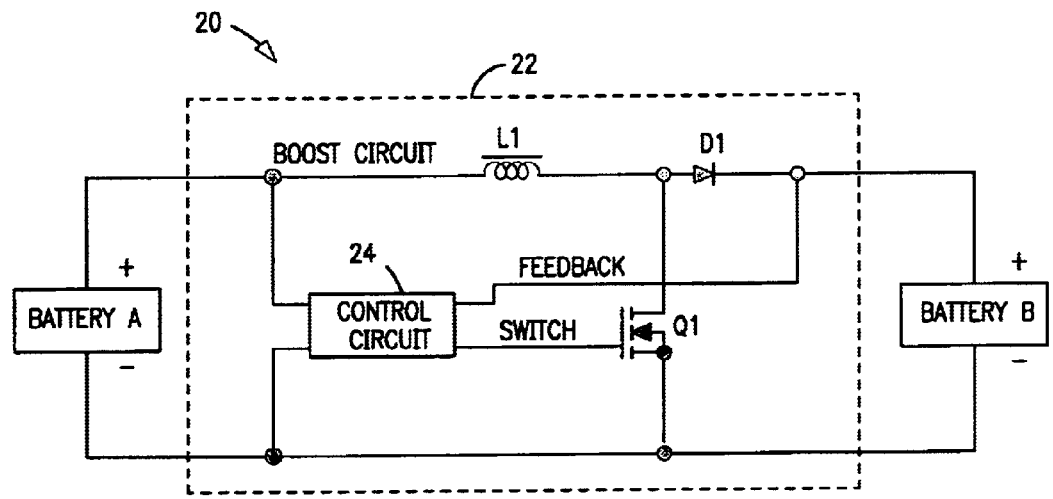
FIG. 3 is a schematic diagram showing another exemplary hybrid battery power source comprising the batteries of FIG. 1 connected by a voltage boost circuit having an inductor and a pulse generating control circuit therein.

Turning now to FIG. 3, another exemplary hybrid battery power source 20 is shown. This power source includes the primary battery "A" and the secondary battery "B" of FIGS. 1 and 2. Battery "A" and battery "B" are connected in parallel but a switching-type voltage boost circuit 22 is interposed between the batteries to charge the secondary battery "B" to a higher potential than the primary battery "A." By way of example, a 2.6-volt Li/SVO or Li/CFx primary battery "A" will have its voltage boosted to about 4 volts for recharging a lithium-ion secondary battery "B." Within the boost circuit 22 is a conventional oscillator-type control circuit 24 that provides variable-width charging pulses to charge the secondary battery "B" to a relatively constant potential even though the voltage level of the primary battery "A" may vary through some range. By way of example, if the primary battery "A" is an Li/SVO or Li/CFx battery and the secondary battery "B" is a lithium-ion battery, the charging voltage on the secondary battery "B" can be maintained at a fairly constant level of about 4 volts even though the output of the primary battery "A" varies between about 2.0 to 3.0 volts during its service life. Thus, within the life of the primary battery "A," every defibrillator discharge will take place at approximately the same energy due to the constant voltage output of the secondary battery "B."

In FIG. 3, the primary battery "A" delivers energy to the input of the boost circuit 22 while the output of the boost circuit 22 is connected to the secondary battery "B." The basic principle of operation for the boost circuit 22 is as follows:

The control circuit 24 derives prime power from the primary battery "A" and includes an oscillator function. The control circuit's output labeled "Switch" is toggled rapidly (e.g. 100 kHz) to turn the field effect transistor Q1 on and off.

Each time that transistor Q1 is turned on, current flow increases in the inductor L1 and energy is imparted to the magnetic field associated with the inductor. A rectifier diode D1 is reverse biased and prevents current flow from the secondary battery "B" backward in to Q1.

When transistor Q1 is turned off, the magnetic field collapses in the inductor L1 and returns the energy to the circuit, causing the voltage across the inductor to increase.

The collapsing magnetic field in the inductor develops a higher positive voltage at the anode of rectifier diode D1. The diode D1 becomes forward biased and current flows from the inductor L1 through the diode and into the secondary battery "B," transferring energy to that battery.

The circuit labeled "Feedback" samples the voltage at the secondary battery "B" and controls the rate of switching of transistor Q1 to regulate the flow of energy to battery "B" and, hence, the charge imparted to that battery.

As indicated, the primary benefit of the hybrid battery power source 20 of FIG. 3 relative to the FIG. 2 design is that the secondary battery "B" can be charged and maintained at a higher working voltage than the primary battery "A," and virtually all of the defibrillator charging circuit energy can be derived from the secondary battery. By using voltage boosting and control circuitry having an inductive component connected between the primary and secondary batteries, increased voltage is delivered to the secondary battery "B" for recharging it to above the voltage of the primary battery "A." Moreover, the charging current is controlled to have a variable pulse width, allowing it to operate over a range of voltages on the primary battery "A," such as about 2.0 volts to 3.0 volts for an Li/SVO or Li/CFx battery, in all cases charging the secondary battery "B" to a higher voltage, such as about 4 volts for a lithium-ion battery. Thus, throughout the life cycle of the primary battery "A," the secondary battery "B" will be delivering the same voltage to charge the capacitors in the defibrillator or ICD. This represents a significant advantage over prior art power sources, both in the short charge time and in the constancy of the charge going to the secondary battery "B." The full charge capacity of the primary battery "A" is thus available. The pulse width of the boost circuit 22 is simply varied to maintain a constant charging voltage on the secondary battery "B" regardless of where the primary battery "A" is in its cycle. Note that for a lithium-ion secondary battery "B" charged to 4 volts and operating at a current of 4 amperes, a five-second charge time is all that would be required to produce a 40 joule pulse. Again, this minimal charge time is a distinct improvement over previous defibrillator batteries.

Figure 4:
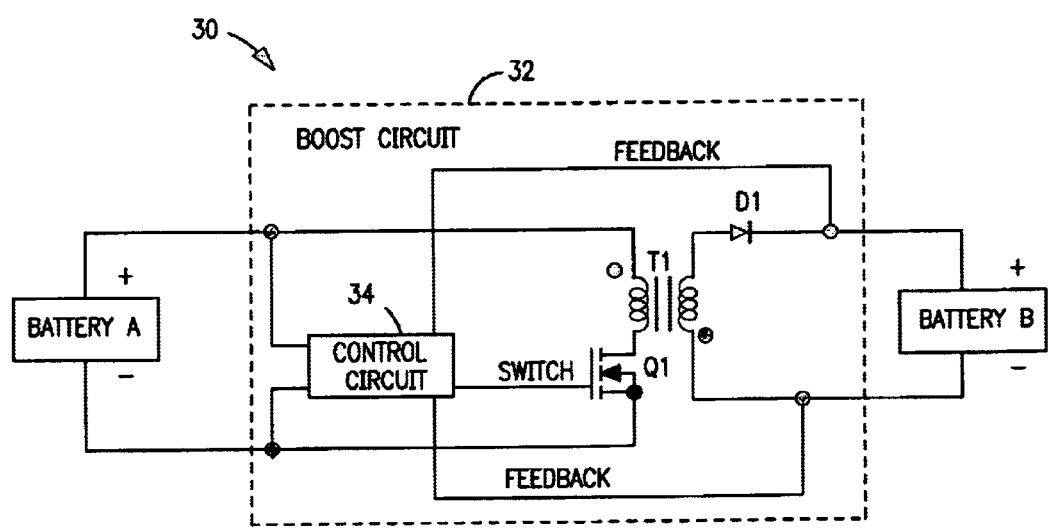
FIG. 4 is a schematic diagram showing another exemplary hybrid battery power source comprising the batteries of FIG. 1 connected by another voltage boost circuit having a flyback transformer and a pulse generating control circuit therein.

Turning now to FIG. 4, another exemplary hybrid battery power source 30 is shown. This power source includes the primary battery "A" and the secondary battery "B" of FIGS. 1 and 2. Battery "A" and battery "B" are connected in parallel with a voltage boost circuit 32 containing a conventional oscillator-type control circuit 34, but with the boost circuit 32 being implemented as a flyback converter. In particular, instead of utilizing a series inductor to boost the charging voltage to battery "B," a transformer T1 with primary and secondary winding connections is used. Although this represents a minor complication in circuitry, it permits complete isolation of the circuits connected to the primary and secondary sides of the transformer. In FIG. 4, the primary battery "A" again provides the prime power for the circuit, and its output is connected to the input of the boost circuit 32. The pulse output of the boost circuit 32 charges the secondary battery "B." The basic principles of operation for the boost circuit 32 are as follows:

The control circuit 34 derives prime power from the primary battery "A" and again includes an oscillator function. The control circuit's output labeled "Switch" is toggled rapidly (e.g. 100 kHz) to turn the field effect transistor Q1 on and off.

Each time that transistor Q1 is turned on, the current in the primary winding of transformer T1 increases and energy is stored in the magnetic field associated with the transformer. The connection of the secondary winding is reversed in the sense that the induced voltage at the anode of rectifier diode D1 is negative, such that the rectifier is reverse biased and no current flows in the secondary winding while the magnetic field is increasing. The number of turns for the secondary winding may be larger than that of the primary in order to provide a voltage boost function.

When the control circuit 34 turns off transistor Q1, the magnetic field begins to collapse, causing voltages of opposite polarity to be induced across both the primary and secondary windings. Because these voltages are opposite in polarity, the anode of diode D1 is driven to a positive polarity, causing this rectifier to conduct and current to flow, thereby delivering energy to secondary battery "B."

The circuits labeled "Feedback" sample the voltage of the secondary battery "B" and are used by the control circuit 34 to vary the rate of switching of transistor Q1. This provides the means to regulate the flow of energy to the secondary battery "B" and, hence, the charge imparted to that battery.

The primary benefit of the hybrid battery power source 30 of FIG. 4 relative to the FIG. 2 design is that the secondary battery "B" may be charged and maintained at a higher working voltage than the primary battery "A." The primary benefit of the hybrid battery power source 30 of FIG. 4 relative to the FIG. 3 design is that the primary and secondary batteries "A" and "B" do not share a common return circuit.

Figure 5:
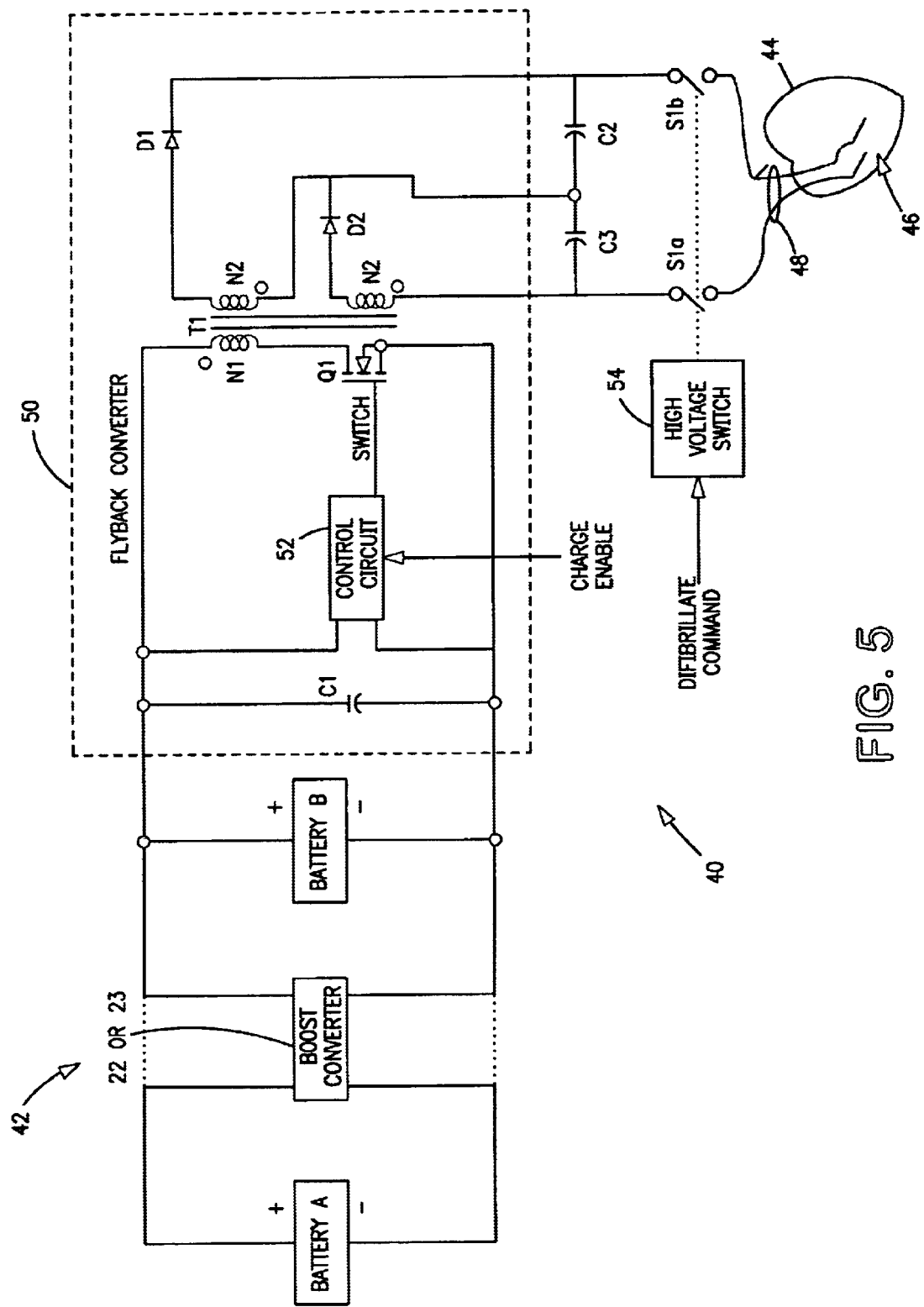
FIG. 5 is a schematic diagram showing a hybrid battery power source of the invention arranged in a defibrillator and discharging into a voltage amplification system.

Turning now to FIG. 5, a battery powered high energy medical device is embodied as a defibrillation system 40 that is shown schematically to include a hybrid battery power source 42 and other circuits and devices for defibrillating a heart 44 using high voltage pulses. The hybrid battery power source 42 includes the primary and secondary batteries "A" and "B" described above. Batteries "A" and "B" are preferably connected in parallel via a voltage boost circuit 22 or 32 as described above relative to FIGS. 3 and 4. Alternatively, the batteries "A" and "B" could be connected directly in parallel, as described above relative to FIG. 2. The defibrillation system-40 includes physiologic electrodes 46 that are attached to cardiac tissue of the heart 44 for the purposes of monitoring cardiac activity and delivering electrical energy in the event that cardiac activity becomes abnormal. The electrodes are connected to the defibrillation system 40 via conventional leads 48. A conventional voltage amplification system or flyback converter circuit 50 having an oscillator-type control circuit 52 therein is also provided as part of the defibrillation system 40. A description of defibrillation operation for the depicted subsystems follows:

Circuitry (not shown) that is part of the defibrillation system 40 will monitor the activity of the cardiac muscle. Should the monitored cardiac activity indicate the need for delivery of a defibrillation charge, the signal labeled "Charge Enable" will be asserted to activate the control circuit 52 that is part of the flyback converter circuit 50. This will begin a capacitor charge sequence for charging energy storage capacitors C2 and C3.

The control circuit 52 derives prime power from the batteries "A" and "B" and includes an oscillator function. Capacitor C1 provides high frequency decoupling and lowers the AC source impedance for the hybrid battery power source 42 to the flyback converter 50. As stated, the hybrid battery power source 42 can be constructed in accordance with any of the embodiments of FIGS. 2, 3 and 4, or modifications thereof. The control circuit output labeled "Switch" is toggled rapidly (e.g. 100 kHz) to turn transistor Q1 on and off.

Each time that the transistor is turned on, the current in the primary winding of transformer T1 increases and energy is stored in the magnetic field associated with the transformer. The connection of the secondary windings is reversed in the sense that the induced voltages at the anodes of rectifier diodes D1 and D2 is negative such that the diodes are reverse biased and noncurrent flows in the secondary windings while the magnetic field is increasing.

When the control circuit 52 turns off transistor Q1 the magnetic field begins to collapse, causing voltages of opposite polarity to be induced across both the primary and secondary windings. Because these voltages are opposite in polarity, the anodes of diodes D1 and D2 are driven to a positive polarity, causing the diodes to conduct and current to flow, delivering energy to energy storage capacitors C2 and C3.

The number of turns N2 and N3 in the secondary windings is much larger than the number of turns N1 of the primary winding, by a ratio of perhaps 100 to 1, in order to achieve a large voltage boost function. Because of the large turns ratio, the low primary winding voltage will be increased to a high secondary winding voltage, the multiplication factor being nearly equal to the turns ratio. In this manner, a four volt prime power source may be increased to hundreds of volts.

The two galvanically isolated secondary windings on transformer T1 have an identical number of turns (N2=N3) and are each connected to energy storage capacitors C2 and C3. This connection causes the capacitors to be simultaneously charged in a parallel manner.

At the completion of the charge cycle, the defibrillation system control circuitry negates the signal labeled "Charge Enable" and asserts the signal labeled "Defibrillate Command." This signal activates the high voltage switch 54 depicted as two switch circuits S1a and S1b. These switch circuits connect the energy storage capacitors C2 and C3 in a series configuration to the wires leading to the physiologic electrodes attached to the cardiac tissue. The energy stored in the capacitors C2 and C3 is rapidly delivered to the heart to provide the therapeutic benefit.

The defibrillator system of FIG. 5 thus utilizes a flyback converter 50 that has primary and secondary transformer windings in the circuit providing isolation from the hybrid battery power source 42. This allows a modification in which multiple transformers can be used, with the primary sides thereof being connected in series or parallel and the secondary sides thereof likewise being connected in series or parallel. This would provide voltage multiplication in case it is desired to charge multiple capacitor banks.

Rationale for Configuration

The configuration of batteries and circuitry described above in connection with the various drawing figures provides an improvement in the performance of implantable defibrillators and ICDs by reducing charge times to manageable and predictable levels. These configurations provide the additional benefit of utilizing the stored energy of the primary battery to maximum extent, thereby increasing the service life for the defibrillator system. As previously described, a fundamental requirement for the power source in an implantable defibrillator/ICD application is the ability to deliver a large amount of energy to the circuitry in order to charge the energy storage capacitors in the shortest time possible. A second requirement of nearly equal importance is the maximum utilization of stored energy within the power source in order to provide maximum service life for the implanted device.

The rate at which power can be delivered from a battery or other electrical energy source to a load is inversely proportional to the internal resistance or impedance of the energy source. This is due to the fact that the load current flows through the internal resistance of the battery and the resulting power is dissipated as waste heat within the battery structure. In order to reduce the time required to charge the energy storage capacitors, the charging circuit must draw higher load current from the battery. Both the Li/SVO and Li/CFX battery chemistries produce an internal resistance that renders them less able to supply high peak currents as well as the lithium-ion battery. This can be seen in Table 1 below.

TABLE 1

| Battery Chemistry | Lithium - CFx (primary) | Lithium - SVO (primary) | Lithium - Ion (rechargeable) |
|---|---|---|---|
| Voltage Range (VDC) | 2.8–2.0 | 3.0–2.0 | 4.0–3.5 |
| Internal Resistance (ohms) | >>1.0 | 0.5–1.0 | 0.1–0.5 |
| Energy Density (Wh/cc) | 0.8–0.9 | 0.40 | 0.2 |

The internal resistance values given above are average values. It will be seen that the internal resistance of the Li/CFx battery chemistry is the highest, and this internal resistance renders such batteries unsuitable for defibrillators and ICDs if used alone. As noted above, the internal resistance of the Li/SVO battery can increase to unacceptable levels during battery run-down. These batteries are thus susceptible to voltage delay effects.

By comparison, the internal resistance of the lithium-ion battery is low and relatively stable. However, it will be seen that its energy density is also substantially lower than that of Li/SVO and Li/CFx batteries. In regard to battery energy density and device service life, it is known that for a given battery volume, the highest energy density battery will possess the largest total energy and will, logically, provide the longest device service life. Based upon energy density, the data in Table 1 indicates that the Li/CFx battery chemistry should provide the longest device service life, with the Li/SVO battery chemistry being the second best. However, as indicated, the internal resistance characteristics of these batteries render them problematic if used alone in a defibrillator or ICD. The lowest energy density of the above-listed battery chemistries is found in the lithium-ion battery. The energy density level is so low that such batteries cannot realistically be used in implantable defibrillators and ICDs, notwithstanding their favorable internal resistance values.

The present invention solves these problems by utilizing two different battery chemistries wherein each battery is utilized in a manner which is optimally matched to its capabilities. An Li/CFx battery or an Li/SVO battery can thus be chosen for the primary energy source (battery "A") because they provide superior total energy for a given battery volume. A lithium-ion battery can be chosen as the energy source for the energy storage capacitors (battery "B") because it provides an internal resistance that is low and relatively stable, and is therefore capable of delivering the highest instantaneous power, providing the shortest charging time for the energy storage capacitors. The embodiments that are taught herein thus provide a clear advantage over single battery systems because each battery is used in an optimum fashion, yielding an implantable defibrillator or ICD with minimum capacitor charging time and maximum device service life.

The present invention is also superior with respect to precise end-of-life determination of the power source. In particular, a monitoring feature could be provided that monitors the voltage level of the primary battery "A." Over time, this voltage level may drop below the level necessary to trigger the voltage boost circuit. Monitoring the voltage level of the primary battery "A" would provide a warning that the secondary battery "B" is no longer being charged. However, if the secondary battery "B" is a lithium-ion cell, it will have a known capacity to deliver some number of defibrillatory pulses, say 100 pulses. It would thus be known that the defibrillator or ICD will work for this remaining number of pulses and steps can be taken to promptly replace the primary battery "A."

Accordingly, a hybrid battery power source for implantable medical use has been disclosed and the objects of the invention have been achieved. It should, of course, be understood that the description and the drawings herein are merely illustrative, and it will be apparent that the various modifications, combinations and changes can be made in accordance with the invention. As such, the invention is not to be in any way limited except in accordance with the spirit of the appended claims and their equivalents.

We claim:

1. A hybrid battery power source for implantable medical use, comprising:
    a primary battery;
    a secondary battery connected to receive power from said primary battery;
    said secondary battery being adapted to power to an implantable medical device designed for high energy electrical stimulation of body tissue for therapeutic purposes; and
    a voltage boost circuit between said primary battery and said secondary battery, said voltage boost circuit being adapted to deliver variable width charge pulses at sufficient voltage to charge said secondary battery, and to regulate charge pulse frequency based on a feedback signal from said secondary battery.

2. A hybrid battery power source in accordance with claim 1, wherein said primary battery has higher energy density than said secondary battery.

3. A hybrid battery power source in accordance with claim 1, wherein said secondary battery has lower internal resistance than said primary battery.

4. A hybrid battery power source in accordance with claim 1, wherein said secondary battery is not subject to voltage delay.

5. A hybrid battery power source in accordance with claim 1, wherein said secondary battery has higher voltage potential than said primary battery.

6. A hybrid battery power source in accordance with claim 1, wherein said primary battery has high energy density and high relatively unstable internal resistance, and wherein said secondary battery has low energy density and low relatively stable internal resistance.

7. A hybrid battery power source in accordance with claim 1, wherein said primary battery is selected from the group consisting of lithium-carbon monofluoride batteries and lithium-silver vanadium oxide batteries, and wherein said secondary battery is selected from the group consisting of lithium-ion batteries.

8. A hybrid battery power source in accordance with claim 1, wherein said primary battery and said secondary battery are interconnected in parallel via said voltage boost circuit.

9. A hybrid battery power source in accordance with claim 8, wherein said voltage boost circuit comprises a charge pulse generating control circuit and an inductive element.

10. A hybrid battery power source in accordance with claim 8, wherein said voltage boost circuit comprises a charge pulse generating control circuit and a flyback transformer.

11. An implantable medical device for high energy electrical stimulation of body tissue for therapeutic purposes, comprising:
   a pair of electrical contacts adapted to provide electrical stimulation to body tissue;
   energy storage means adapted to provide electrical energy to said electrical contacts;
   switching means adapted to periodically interconnect said energy storage means to said electrical contacts; and
   a hybrid battery power source adapted to provide power to said energy storage means and including:
   a primary battery;
   a secondary battery connected to receive power from said primary battery and to provide power to said energy storage means; and
   a voltage boost circuit between said primary battery and said secondary battery, said voltage boost circuit being adapted to deliver variable width charge pulses at sufficient voltage to charge said secondary battery, and to regulate charge pulse frequency based on a feedback signal from said secondary battery.

12. An implantable medical device in accordance with claim 11, wherein said primary battery has higher energy density than said secondary battery.

13. An implantable medical device in accordance with claim 11, wherein said secondary battery has lower internal resistance than said primary battery.

14. An implantable medical device in accordance with claim 11, wherein said secondary battery is not subject to voltage delay.

15. An implantable medical device in accordance with claim 11, wherein said secondary battery has higher voltage potential than said primary battery.

16. An implantable medical device in accordance with claim 11, wherein said primary battery has high energy density and high relatively unstable internal resistance, and wherein said secondary battery has low energy density and low relatively stable internal resistance.

17. An implantable medical device in accordance with claim 11, wherein said primary battery is selected from the group consisting of lithium-carbon monofluoride batteries and lithium-silver vanadium oxide batteries, and wherein said secondary battery is selected from the group consisting of lithium-ion batteries.

18. An implantable medical device in accordance with claim 11, wherein said primary battery and said secondary battery are interconnected in parallel via said voltage boost circuit.

19. An implantable medical device in accordance with claim 18, wherein said voltage boost circuit comprises a charge pulse generating control circuit and an inductive element.

20. An implantable medical device in accordance with claim 18, wherein said voltage boost circuit comprises a charge pulse generating control circuit and a flyback transformer.

21. A method for powering an implantable medical device designed for high energy electrical stimulation of body tissue for therapeutic purposes, comprising:
   providing a primary power source;
   providing a secondary power source and connecting it to receive power from said primary power source;
   connecting said secondary power source to power said implantable medical device designed; and
   providing a voltage boost circuit between said primary battery and said secondary battery, said voltage boost circuit being adapted to deliver variable width charge pulses at sufficient voltage to charge said secondary battery, and to regulate charge pulse frequency based on a feedback signal from said secondary battery.

22. A method in accordance with claim 21, wherein said primary power source has higher energy density than said secondary battery.

23. A method in accordance with claim 21, wherein said secondary battery has lower internal resistance than said primary battery.

24. A method in accordance with claim 21, wherein said secondary battery is not subject to voltage delay.

25. A method in accordance with claim 21, wherein said secondary battery has higher voltage potential than said primary battery.

26. A method in accordance with claim 21, wherein said primary battery has high energy density and high relatively unstable internal resistance, and wherein said secondary battery has low energy density and low relatively stable internal resistance.

27. A method in accordance with claim 21, wherein said primary battery is selected from the group consisting of lithium-carbon monofluoride batteries and lithium-silver vanadium oxide batteries, and wherein said secondary battery is selected from the group consisting of lithium-ion batteries.

28. A method in accordance with claim 21, wherein said primary battery and said secondary battery are interconnected in parallel via said voltage boost circuit.

29. A method in accordance with claim 28, wherein said voltage boost circuit comprises a charge pulse generating control circuit and an inductive element.

30. A method in accordance with claim 28, wherein said voltage boost circuit comprises a charge pulse generating control circuit and a flyback transformer.

* * * * *

UNITED STATES PATENT AND TRADEMARK OFFICE
CERTIFICATE OF CORRECTION

PATENT NO. : 6,909,915 B2
DATED : June 21, 2005
INVENTOR(S) : Wilson Greatbatch et al.

It is certified that error appears in the above-identified patent and that said Letters Patent is hereby corrected as shown below:

Column 10,
Line 49, change "power to an" to -- power an --.

Column 12,
Line 26, delete "designed.".

Signed and Sealed this

Twenty-second Day of November, 2005

JON W. DUDAS
*Director of the United States Patent and Trademark Office*